(12) United States Patent
Pichon et al.

(10) Patent No.: US 8,630,470 B2
(45) Date of Patent: Jan. 14, 2014

(54) RADIOLOGICAL IMAGERY METHOD MAKING A ZONE OF INTEREST IN AN ORGAN CORRESPOND TO AN ASSOCIATED PART OF THE NETWORK

(75) Inventors: Eric Pichon, Versailles (FR); Yves Trousset, Palaiseau (FR); Jerome Knoplioch, Neuilly sur Seine (FR)

(73) Assignee: General Electric Comany, Schenectady, NY (US)

( * ) Notice: Subject to any disclaimer, the term of this patent is extended or adjusted under 35 U.S.C. 154(b) by 966 days.

(21) Appl. No.: 11/937,734

(22) Filed: Nov. 9, 2007

(65) Prior Publication Data
US 2008/0125640 A1   May 29, 2008

(30) Foreign Application Priority Data

Nov. 24, 2006  (FR) ..................................... 06 10298

(51) Int. Cl.
*G06K 9/00*   (2006.01)

(52) U.S. Cl.
USPC .......................................... 382/131; 600/407

(58) Field of Classification Search
USPC .......................................... 382/131; 600/407
See application file for complete search history.

(56) References Cited

U.S. PATENT DOCUMENTS

| 6,690,816 B2 * | 2/2004 | Aylward et al. | 382/128 |
| 7,831,289 B2 * | 11/2010 | Riker et al. | 600/407 |
| 8,090,164 B2 * | 1/2012 | Bullitt et al. | 382/128 |

OTHER PUBLICATIONS

Pichon, Eric & Tannenbaum, Allen; "Curve Segmentation Using Directional Information, Relation to Pattern Detection", Georgia Institute of Technology, 2005.
Pichon, Eric, Westin, Carl-Fredrik, Tannenbaum, Allen: "A Hamilton-Jacobi-Bellman approach to high angular resolution diffusion tractography", Georgia Institute of Technology and Harvard Medical School, 2005.

* cited by examiner

*Primary Examiner* — David Zarka
*Assistant Examiner* — Katrina Fujita
(74) *Attorney, Agent, or Firm* — Global Patent Operation; Mark A. Conklin

(57) ABSTRACT

Embodiments of the invention relate to a method of processing a radiological image of an organ, the organ being connected to a flow circulation network, and comprising steps according to which:
   an operator or a processing means defines a contour to delimit a zone of interest in the radiological image of the organ;
   the processing means determines part of the network in which the flow supplies the zone of interest or originates from this zone of interest; and
   a display means displays the determined part of the network.

9 Claims, 8 Drawing Sheets

RADIOLOGICAL IMAGERY METHOD MAKING A ZONE OF INTEREST IN AN ORGAN CORRESPOND TO AN ASSOCIATED PART OF THE NETWORK

FIELD OF THE INVENTION

The field of the invention relates to the domain of radiological imagery, and more particularly the domain of operational radiological imagery.

STATE OF THE ART

Operational radiology denotes surgical operation techniques in which a radiologist displays images of an organ provided by an imagery apparatus to guide or control an operation on this organ.

These techniques are particularly useful for performing surgical operations that follow natural circulation pathways in the body (for example the blood, bile and lymph networks) to access a zone to be treated. The surgeon introduces a catheter into a vein or artery until reaching an appropriate point, using an image output by the imagery apparatus.

These techniques have the advantage that they are not very invasive compared with traditional surgical techniques.

For example, operational radiology can be used to treat a target tissue zone by injecting a substance or by closing off a vessel at a given point in the vascular network irrigating the zone to be treated.

The radiologist can inject ethanol to treat a cancerous tumour.

For chemical embolisation, the surgeon injects an embolic agent and also a toxic substance in a vessel that irrigates the target zone. The effects of the embolic agent and the toxic substance combine such that the substance is concentrated as it is routed to the target zone, and also that supply to this zone is cut off.

This type of operation focuses the treatment action on the target zone, thus increasing the treatment efficiency while minimising secondary effects.

In this type of operation, the radiologist must access an operation point that will give an optimum result, in other words treatment of the entire target zone and also limitation of the impact of the operation on the surrounding tissues. To achieve this, the radiologist makes use of the image output by the imagery apparatus and guides the catheter as a function of his experience. The radiologist must identify all vessels supplying the target zone, displaying pre or per operative images.

This task is usually difficult because there may be a very large number of vessels that are difficult to distinguish on the images.

At the same time, in the domain of traditional surgery, software is available to identify eight predetermined regions called the "Couinaud segments", on a radiological image of the liver. Each of these segments is associated with an independent vascularisation and bile drainage system. The precise location of a pathology in one or several of these segments makes ablation of the segment(s) concerned possible without damaging adjacent segments.

However, targeted treatment of a pathology is impossible with this type of operation, because it necessarily leads to ablation of a complete segment.

SUMMARY OF THE INVENTION

One purpose of embodiments of the invention is to describe a tool to be used to help an operator, for example a radiologist, identify his position in a flow circulation network in order to make a local treatment of a given target zone.

Firstly, this problem is solved in the framework of this invention due to a method of processing a radiological image of an organ, the organ being connected to a flow circulation network. An embodiment of the method may include:
  defining with an operator or a processing means a contour to delimit a zone of interest in the radiological image of the organ;
  determining with the processing means part of the flow circulation network wherein the flow supplies the zone of interest or originates from this zone of interest; and
  displaying on a display means the determined part of the network This method can make part of the network correspond with a zone of interest delimited by the operator.

This method allows the operator to identify the part of the network that participates in supplying or leaving the zone of interest, and only this zone.

This method provides an aid tool to help the operator to decide on one or several operation point(s) to treat the zone of interest and to guide a tool to these points.

In particular, embodiments of the method may have the following characteristics:
  the processing means controls the display means to display an image of the organ and/or the flow circulation network on which the determined part of the network is highlighted,
  the processing means controls the display means to display an image of the organ and/or the flow circulation network on which the intensity of the pixels corresponding to the determined part of the flow circulation network is increased,
  the processing means controls the display means to display an image of the organ and/or the flow circulation network on which the pixels corresponding to the determined part of the flow circulation network have a predetermined colour that contrasts with the colours of the other pixels in the image.

Secondly, the problem is also solved due to an embodiment of a second method of processing a radiological image of an organ, the organ being connected to a flow circulation network. The second method may include:
  defining with an operator or a processing means a point or a branch on the circulation network;
  determining with the processing means one or several zones of the organ supplied by the flow passing through the point or the branch defined by the operator, or from which the flow originates; and
  displaying on a display means the determined zone(s) of the organ.

This method can make a zone of the organ correspond with a point or a branch of the network selected by the operator.

With this method, the operator can identify the zone in the organ supplied by the flow passing through the point or the branch of the network that he selected, or the zone from which the flow originates, and only this zone.

This method provides an aid tool to help the operator control the impact on the organ of an operation at a given point in the network. The operator can display the zone of the organ that will be affected by the operation.

In particular, embodiments of the second method may have the following characteristics:
  the processing means controls the display means to display an image of the organ and/or the network on which the intensity of the pixels corresponding to the determined zone of the organ is increased; and the processing means controls the display means to display an image of the organ and/or the network on which the pixels corresponding to the determined zone of the organ have a predetermined colour that contrasts with the colour of the other pixels in the image.

In embodiments of the first method the processing means may determine a direction of circulation of flow in different branches of the network, and the processing means may determine correspondences between points in the organ and one or more branches in the network, as a function of the flow circulation direction.

In one embodiment of this method, the processing means determines a direction of circulation of flow in the different branches of the network by an analysis of the variation of a radius of the branch along each branch.

The method may include a preliminary step in which the processing means applies an algorithm to the image of the organ to determine the pattern of the network to identify different branches making up the network.

The method may be applied to a radiological image that is a composite image composed of several images acquired by different techniques and/or at different instants.

In particular, the radiological image may be a composite image composed of a first image acquired by X-ray tomography and a second image acquired by positron emission tomography, the resulting composite image displaying both the vascular network that supplies the organ and an active zone of a tumour.

An embodiment of the invention is also applicable to a computer program product that can be loaded into a memory of a radiological imagery device comprising a processing means and a display means, to execute steps in the methods described above.

Finally, embodiments of the invention is applicable to a device for processing a radiological image comprising a processing means and a display means, the processing means being programmed to execute the steps in the methods described above.

DETAILED DESCRIPTION OF PREFERRED EMBODIMENTS

Figure 1:
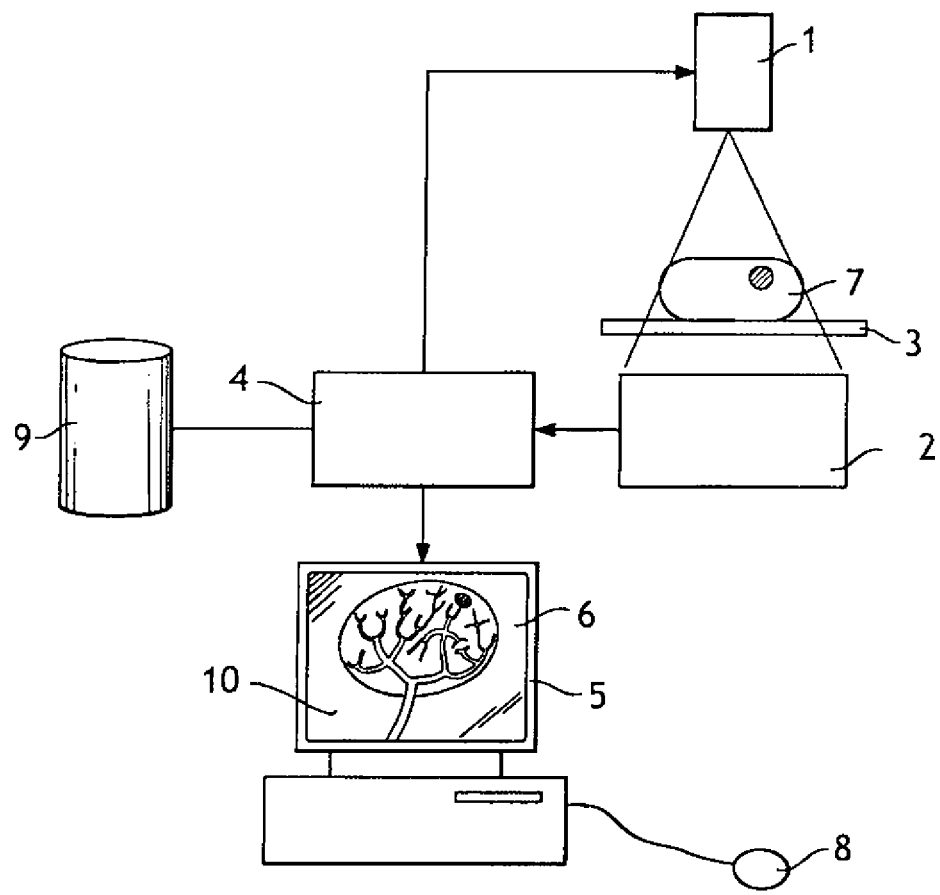
FIG. 1 schematically shows an imagery apparatus.

The imagery apparatus shown in FIG. 1 comprises a source 1 capable of emitting an X-ray beam 8, a detector 2 placed facing the source 1 and capable of detecting rays emitted by source 1, a support 3 placed between the source 1 and the detector 2.

The support 3 may receive an organ 7 for which an image is to be acquired.

The apparatus comprises a processing unit 4 (for example a computer) capable of receiving data supplied by the detector 2 and that can control the source 1 and the detector 2. The treatment unit 4 can control the emission of X-rays by the source and reading of an image by the detector 2.

The apparatus comprises an interface unit 5 comprising a screen 6 and control means including a mouse 8.

Finally, the apparatus comprises a database 9 in which images of the organ 7 that were previously acquired are saved.

The processing unit 4 can control the interface unit so that the interface unit displays an image of the organ 7 acquired in real time or an image of the organ 7 pre-recorded in the database 9.

Figure 3:
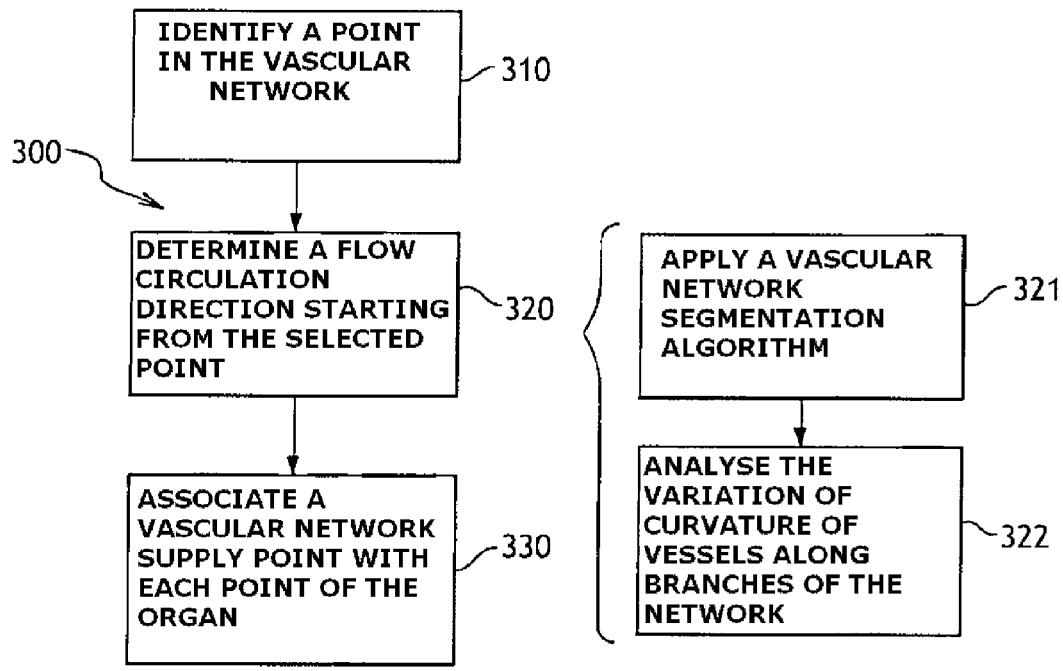
FIG. 3 is a diagram schematically showing steps in a image processing method according to one embodiment of the invention.
Figure 4:
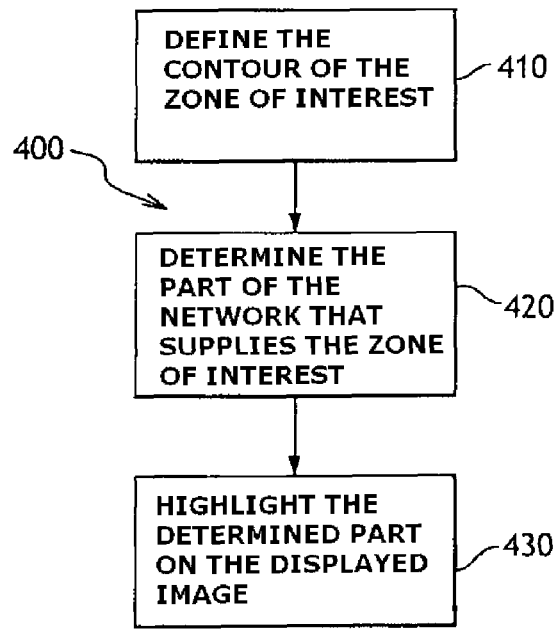
FIG. 4 is a diagram schematically showing steps in an image display method that a surgeon would use to display part of the vascular network that supplies a zone of interest in an organ.
Figure 5:
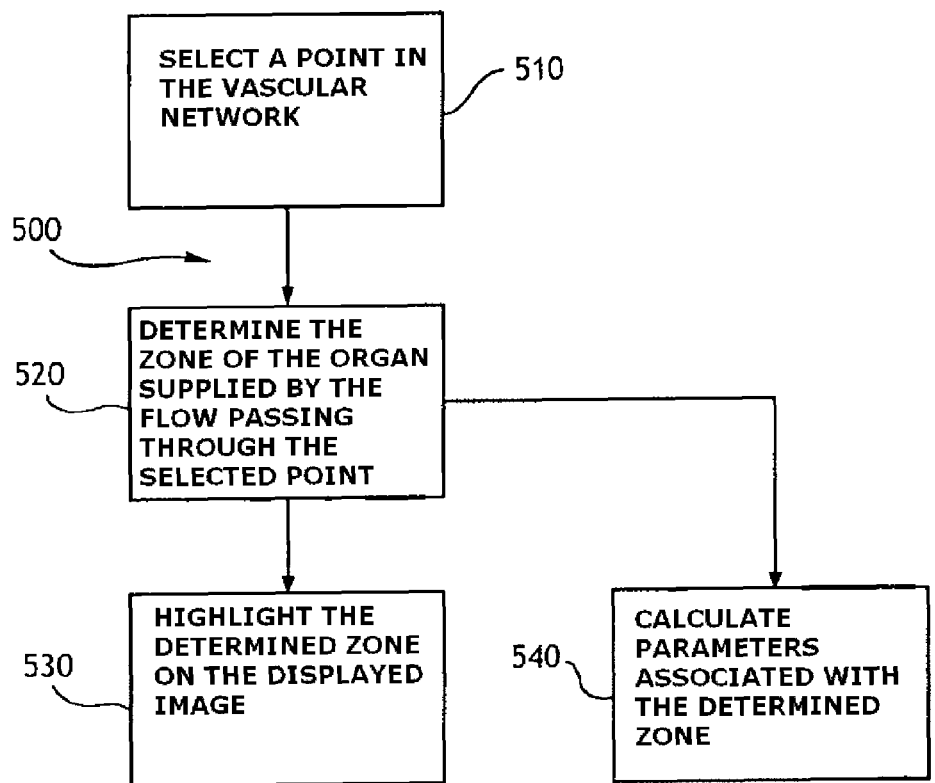
FIG. 5 is a diagram schematically showing steps in an image display method that a surgeon can use to display part of the organ supplied from a point in the vascular network.

The processing unit 5 is programmed to execute an imagery method that comprises the steps represented in FIGS. 3 to 5.

Figure 2:
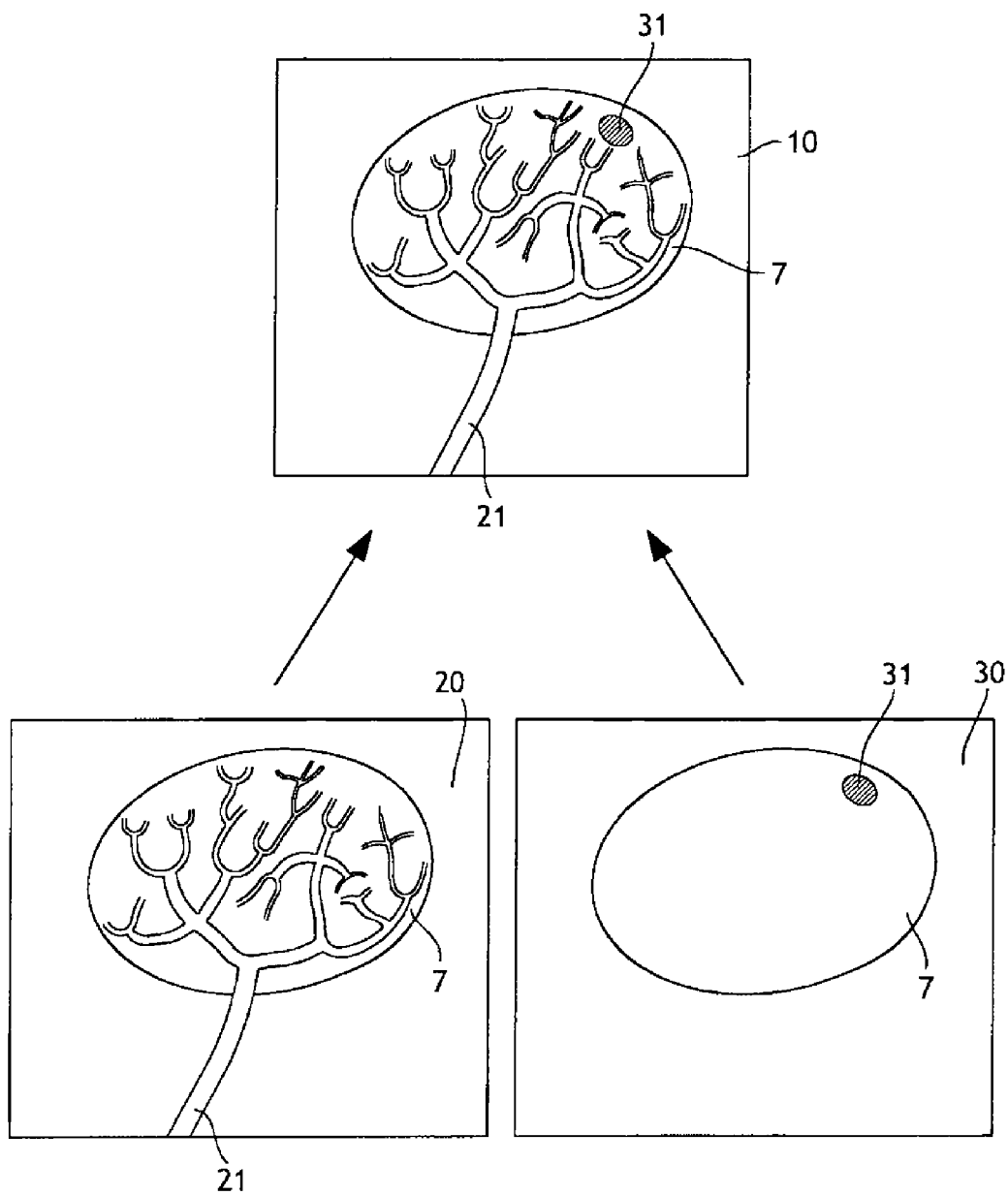
FIG. 2 schematically shows an image of an organ as it could be obtained using an imagery apparatus according to FIG. 1.

FIG. 2 schematically represents an image 10 of the organ 7 as it might be displayed on the screen of the imagery apparatus.

For example, the image 10 is a three-dimensional composite image resulting from the combination of a first three-dimensional image 20 of the organ obtained by X-ray tomography (CT) and a second three-dimensional image 30 of the organ 7 obtained by positron emission tomography (PET). The composed image 10 shows a vascular network 21 that supplies the organ 7 (shown in the first image 20) and an active zone 31 of a tumour (appearing in the second image 30).

The vascular network 21 is composed of vessels forming branches connected to each other. The network 21 has a ramified structure, in other words it comprises main branches onto which secondary branches are connected, each secondary branch being supplied by a single main branch.

FIG. 3 is a diagram schematically representing steps in the image processing method 300.

Figure 3A:
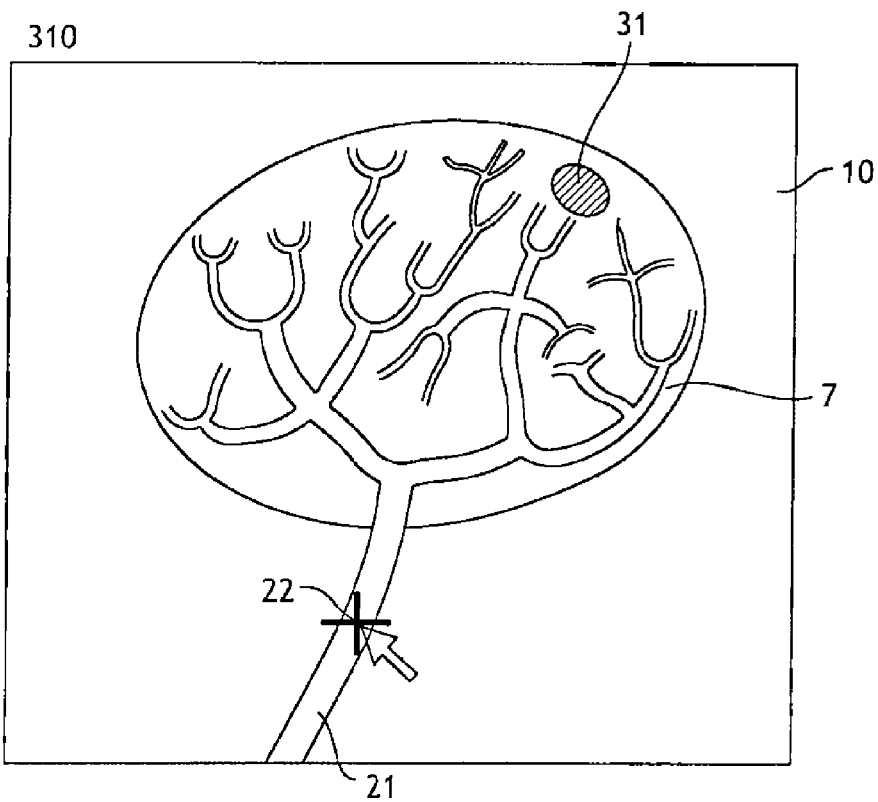
FIGS. 3A to 3C illustrate steps in the method in FIG. 3.

According to a first step 310, an operator selects a point 22 in the vascular network 21 on the displayed image 10. He does this by clicking on the point 22 with the mouse 8 (FIG. 3A).

Figure 3B:
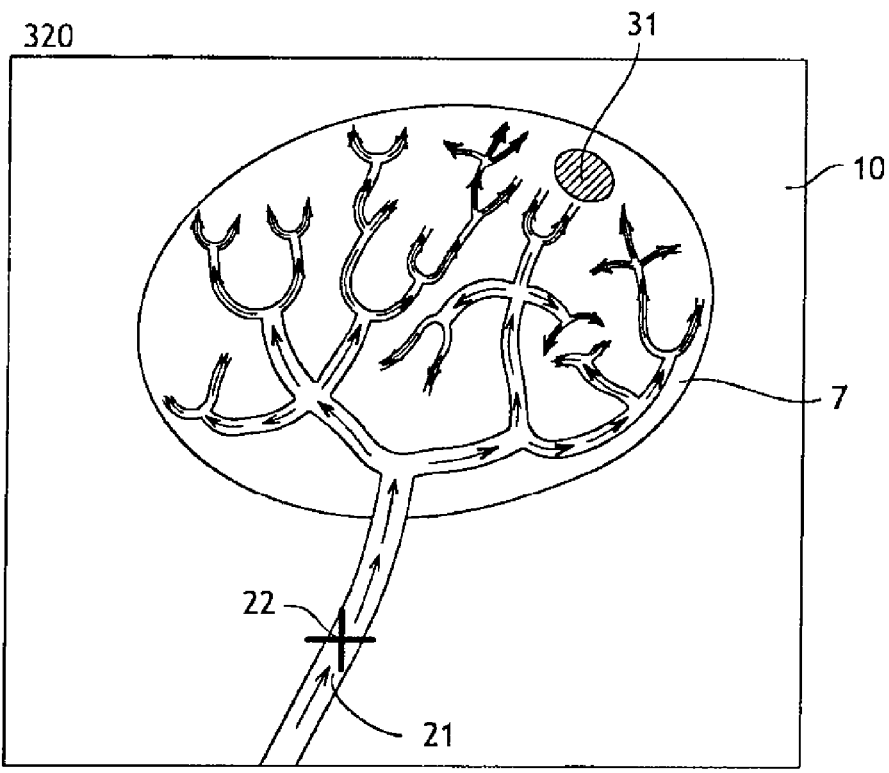

According to a second step 320, the processing unit 4 analyses the first image 20 so as to determine the circulation direction of a blood flow in the vascular network 21 (shown in FIG. 3B by arrows).

This second step 320 includes the following sub-steps:

According to a first sub-step 321, the processing unit applies an algorithm to determine the pattern of the vascular network to the image 20, in other words the different branches that make up the vascular network.

For example, this type of algorithm is described in the "*Curve segmentation using directional information, relation to pattern detection*" publication, Eric Pichon, Allen Tannenbaum, IEEE International Conference on Image Processing (ICIP), volume 2, pages 794-797, 2005.

Then, according to a second sub-step 322, the processing unit determines a variation of a radius of a blood vessel by running along the length of the branch. The flow circulation direction is the direction in which the radius of the vessel decreases along the branch.

Figure 3C:
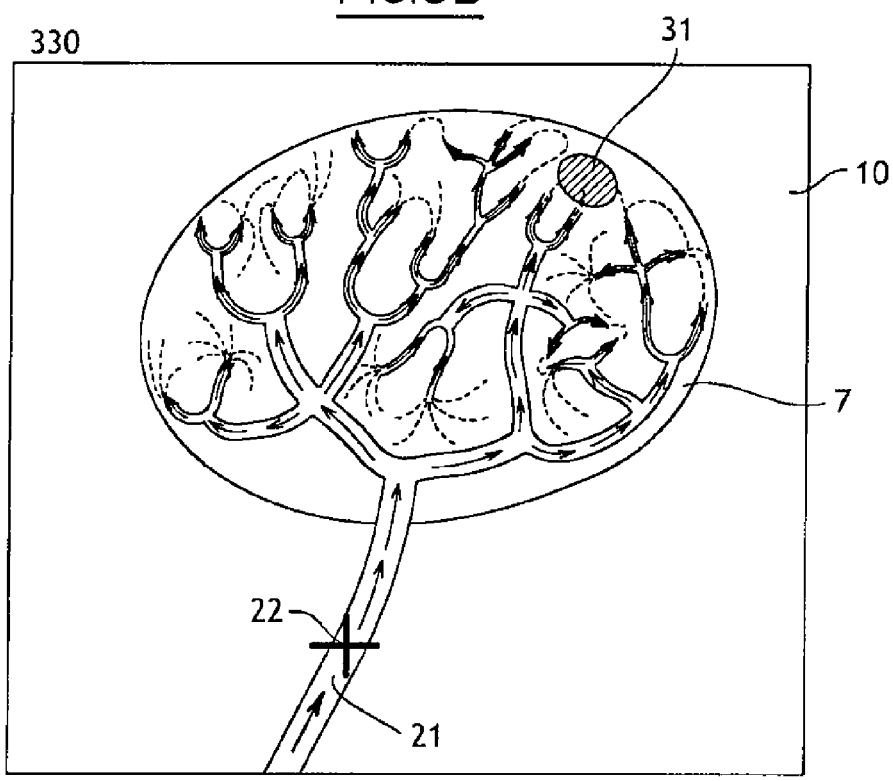

According to a third step 330, the processing unit associates a termination of the vascular network that supplies this point, with each point in the organ 7 (FIG. 3C). For example, this step is done using an algorithm based on a mathematical model of blood distribution through the tissues of the organ starting from the vascular network (shown in dashed lines in FIG. 3C).

The method illustrated in FIGS. 3 and 3A to 3C is used to build up an irrigation map of the organ 7. More precisely, the effect of this method is to determine a blood flow circulation direction in each branch of the network 21 and to associate one or several branches with each point on the image of the organ 7.

FIG. 4 is a diagram schematically showing steps in an image display method 400 allowing an operator to display part of the vascular network that supplies a zone of interest of an organ.

According to a first step 410, the operator defines a contour 32 to delimit a zone of interest in the image 10.

Figure 4A:
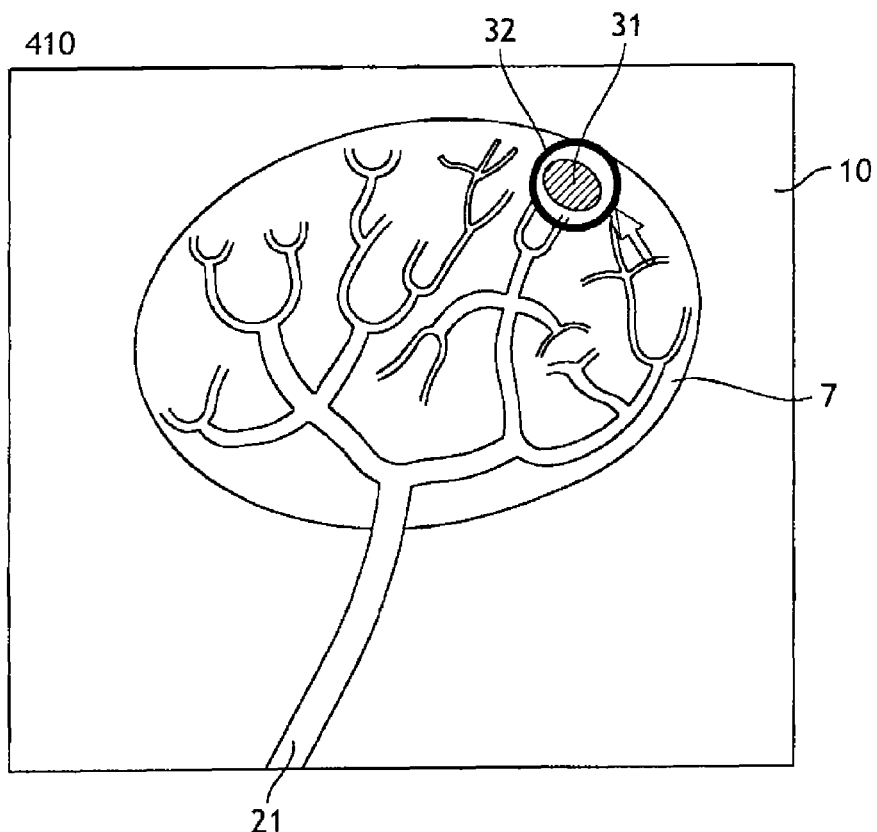
FIGS. 4A to 4C illustrate the steps in the method in the FIG. 4.

To achieve this, the operator uses the mouse 8, for example, to delimit the tumour 31 that appears on the image 10 displayed on the screen (FIG. 4A).

In a second step 420, the processing unit 4 determines a part of the network in which the blood flow that supplies the zone of interest circulates, and only this part.

Figure 4B:
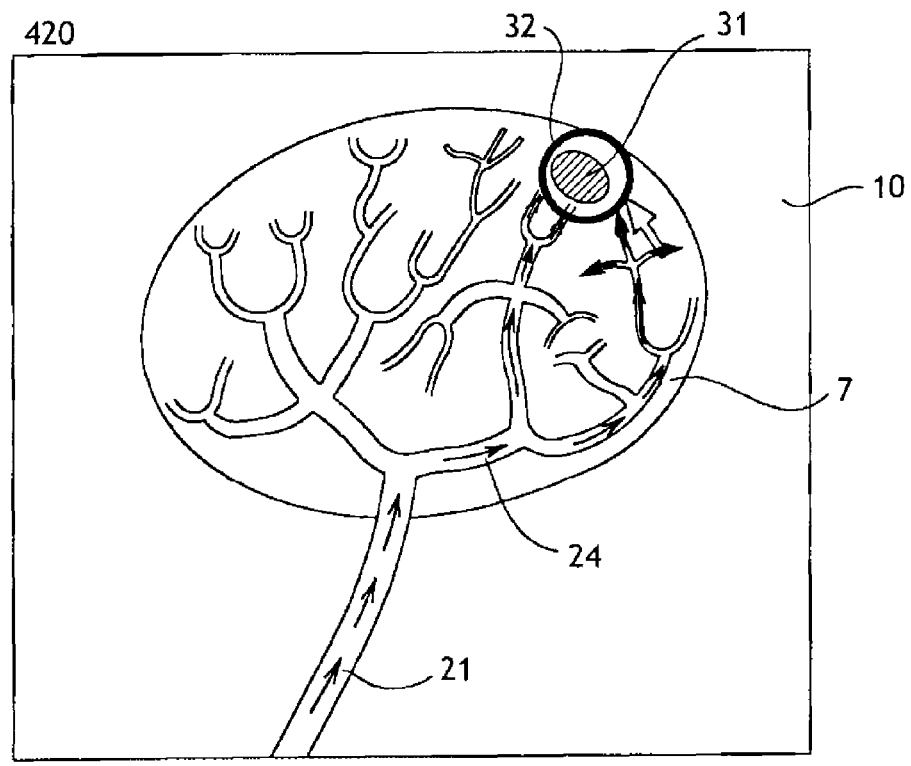

To achieve this, the processing unit identifies all terminations in the blood network that are associated with points contained in the zone of interest. The processing unit then starts from the terminations and works along the vessels along the direction opposite to the direction of blood flow, to determine all vessels that supply the zone of interest (FIG. 4B).

Figure 4C:
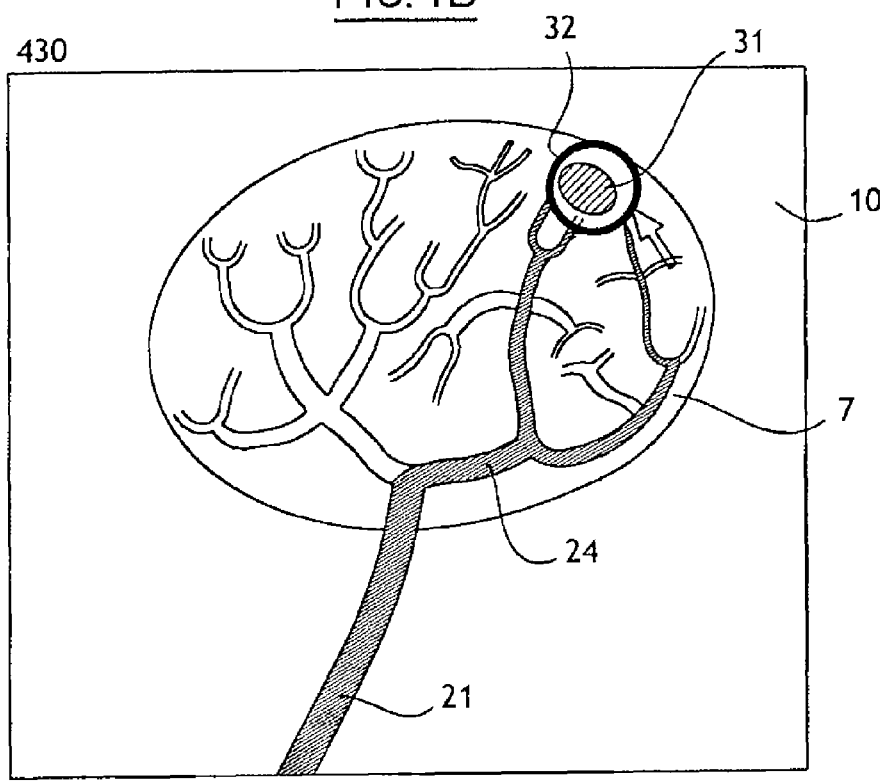

According to a third step 430, the processing unit controls the screen to display the part of the network thus determined on the displayed image 10 (FIG. 4C).

According to a first feature, the processing unit increases the intensity of the pixels corresponding to the determined part of the network, on the displayed images 10 (using a colour that is different from the colours used to display the rest of the image).

According to a second feature, the processing unit controls the display of the part of the network in a specific colour (a colour that is different from the colours used to display the rest of the image).

This third step 430 highlights the part of the network irrigating the zone of interest on the displayed image 10.

The operator can use this method to isolate and display the anatomy of the part of the blood circulation network that participates in supplying the zone of interest, and only this part.

This method provides a tool to aid the operator in deciding on one or several operating points for treatment of the tumour 12 and the access path(s) to these points.

FIG. 5 is a diagram schematically showing the steps in an image display method 500 that an operator can use to display a part of the organ supplied by a point in the vascular network.

In a first step 510, the operator selects a point 23 in the vascular network.

Figure 5A:
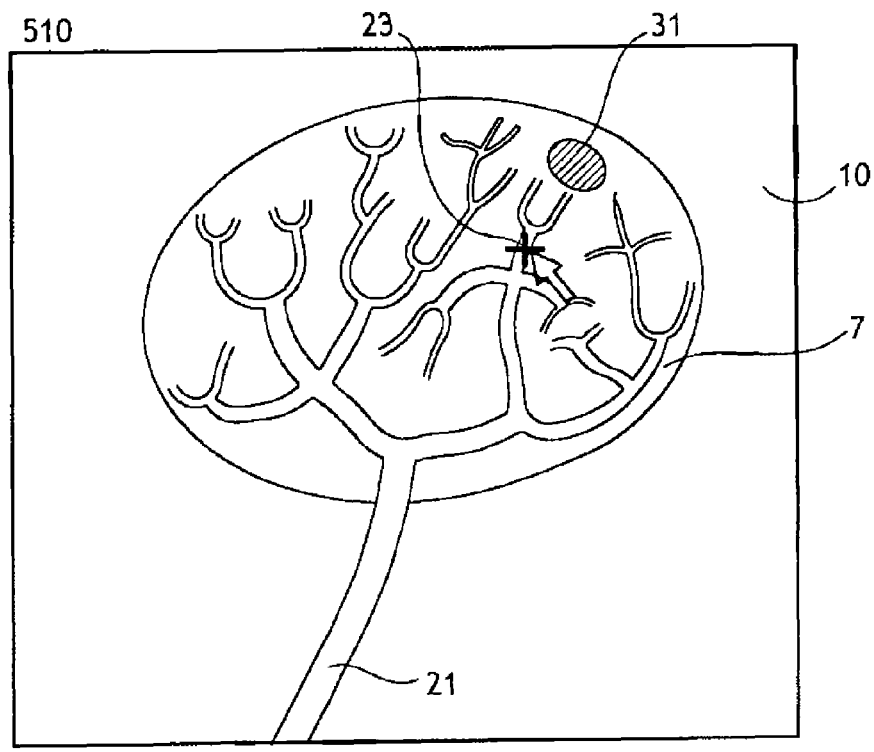
FIGS. 5A to 5C illustrate steps in the method in FIG. 5.

To achieve this, the operator for example uses the mouse 8 to select a point 22 in the vascular network 21, on the screen (FIG. 5A).

In a second step 520, the processing unit 4 determines a zone 32 of the organ supplied by the blood flow passing through the point 23 defined by the operator.

Figure 5B:
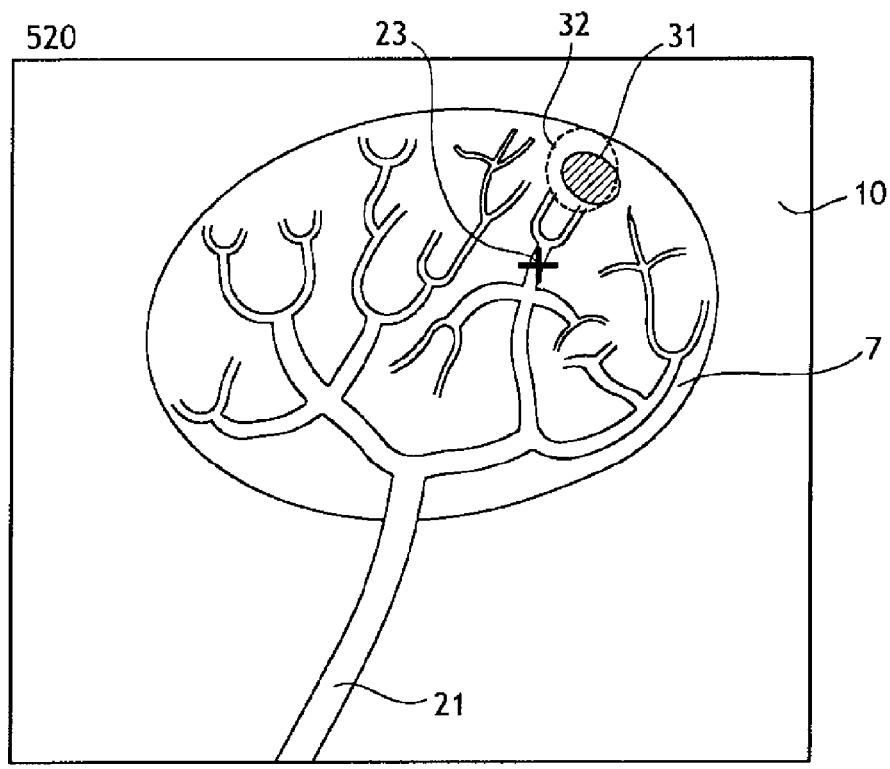

To achieve this, the processing unit starts from point 23 and works along the direction of circulation of the flow along the vessels, and identifies all branches in the blood circulation network that are supplied by point 23 (FIG. 5B). A zone 32 of the organ supplied by the flow is then determined by the processing unit starting from these branches.

According to a third step 530, the processing unit controls the screen to highlight the determined zone 32 of the organ on the displayed image 10 (FIG. 5D).

According to a first feature, the processing unit increases the intensity of the pixels corresponding to the determined zone of the organ, on the displayed image 10.

According to a second feature, the processing unit displays the zone of the organ in a special colour.

This third step can highlight the zone in the organ concerned by the supply point selected by the operator.

According to a fourth step 540, the processing unit calculates parameters associated with the determined zone 32 and controls the display of these parameters on the display means.

Figure 5C:
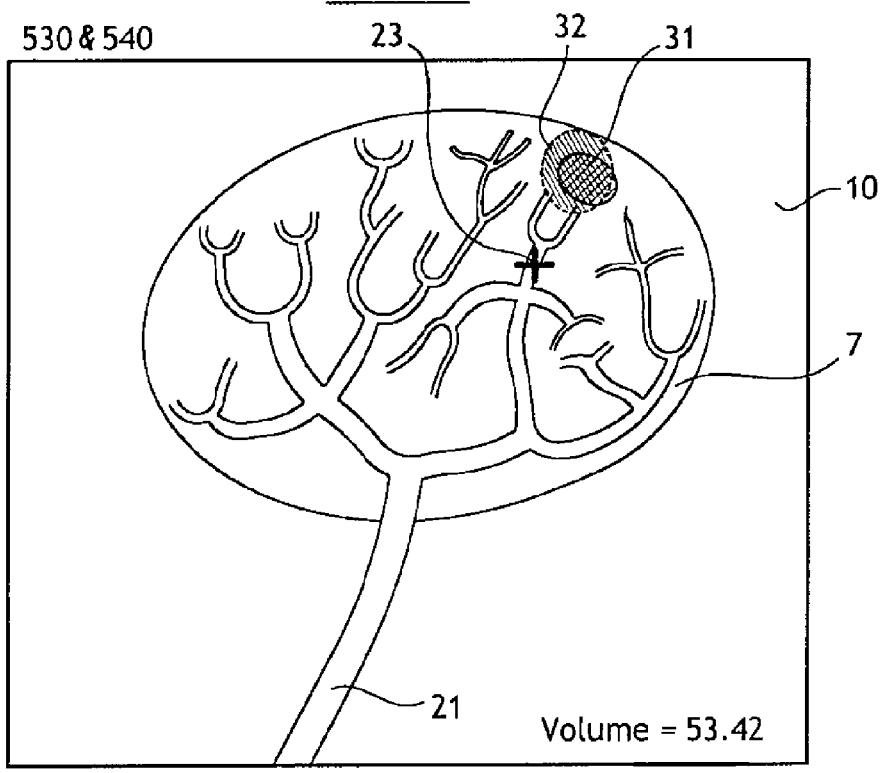

For example, the processing unit estimates the volume of the zone 32 (FIG. 5C).

The operator uses this method to isolate and display the zone in the organ supplied by the blood flow passing through the point in the network that he selected, and only this zone.

This method provides an operator aid tool that helps the operator check the impact on the organ of an operation at a given point in the network. The operator can display the zone of the organ that will be affected by the operation, and can also obtain information about anatomical parameters related to this zone.

The operator can use the method 500 to select one or several points in the network, or one or several branches in the network (for example arteries) and make selected points or selected branches correspond to one or several zones of the organ. In particular, these zones may be highlighted in the image in different colours, in which each colour identifies a zone associated with a particular supply point or a particular branch in the network.

An embodiment of the invention has been described in which the circulation network is a vascular network in which blood circulates to supply an organ. Obviously, the method is applicable to other types of networks in which fluids circulate in a similar manner, including supply and drain networks, for example such as a bile network, a lymph network, an air circulation network, a urine network, etc. The method may also be applied to other types of networks, for example such as a nerve network in which nerve pulses circulate (or propagate).

What is claimed is:

1. A method of processing a radiological image of an organ, the organ being connected to a flow circulation network, the method comprising:
    defining a contour to delimit a zone of interest of the organ in the radiological image of the organ;
    identifying and associating, via a processor, at least a part of the flow circulation network with the zone of interest that the flow circulation network supplies blood to, or which originates from the zone of interest;
    the step of identifying comprising:
    identifying all terminations in the flow circulation network associated with points contained in the zone of interest;
    starting from the terminations and working opposite a direction of blood flow,
    identifying at least one vessel of the flow circulation network supplying blood flow to the zone of interest; and
    isolating and displaying on a display the zone of interest of the organ and displaying and highlighting the associated part of the network.

2. The method of claim 1, wherein an intensity of pixels corresponding to the associated part of the network is increased.

3. The method of claim 1, wherein pixels corresponding to the associated part of the network have a predetermined color that contrasts with the colors of other pixels in the image.

4. The method of claim 1, wherein the defining a contour to delimit a zone of interest being performed with an operator or the processor.

5. The method of claim 4, wherein the processor determines a direction of circulation of flow in different branches of the flow circulation network, and wherein the processing unit determines correspondences between points in the organ and one or more branches in the flow circulation network, as a function of the flow circulation direction.

6. The method of claim 5, wherein the processor determines a direction of circulation of flow in different branches of the flow circulation network by an analysis of the variation of a radius of the branch along each branch.

7. The method of claim 4, wherein the processor applies an algorithm to the image of the organ to determine a pattern of the flow circulation network to identify different branches making up the network.

8. The method of claim 4, wherein the radiological image is a composite image composed of several images acquired by different techniques and/or at different instants.

9. The method of claim 4, wherein the radiological image is a composite image composed of a first image acquired by X-ray tomography and a second image acquired by positron emission tomography, the resulting composite image displaying both the flow circulation network that supplies the organ and an active zone of a tumor.

* * * * *

UNITED STATES PATENT AND TRADEMARK OFFICE
CERTIFICATE OF CORRECTION

PATENT NO.        : 8,630,470 B2                                             Page 1 of 1
APPLICATION NO.   : 11/937734
DATED             : January 14, 2014
INVENTOR(S)       : Pichon et al.

It is certified that error appears in the above-identified patent and that said Letters Patent is hereby corrected as shown below:

On the Title Page, (73), under "Assignee", in Column 1, Line 1, delete "Comany," and insert -- Company, --, therefor.

Signed and Sealed this
Seventh Day of April, 2015

Michelle K. Lee
*Director of the United States Patent and Trademark Office*